United States Patent
Eslami et al.

(10) Patent No.: US 10,182,714 B2
(45) Date of Patent: Jan. 22, 2019

(54) METHOD FOR CORRECTING AN OCT IMAGE AND COMBINATION MICROSCOPE

(71) Applicant: Carl Zeiss Meditec AG, Jena (DE)

(72) Inventors: Abouzar Eslami, Munich (DE); Konstantinos Filippatos, Munich (DE); Corinna Maier-Matic, Neuried (DE); Christine Kochwagner, Rott am Inn (DE); Thomas Schuhrke, Munich (DE); Guenter Meckes, Munich (DE); Stefan Duca, Poing (DE); Carolin Schiele, Aufhausen (DE); Falk Hartwig, Munich (DE)

(73) Assignee: Carl Zeiss Meditec AG, Jena (DE)

( * ) Notice: Subject to any disclaimer, the term of this patent is extended or adjusted under 35 U.S.C. 154(b) by 235 days.

(21) Appl. No.: 14/866,342

(22) Filed: Sep. 25, 2015

(65) Prior Publication Data
US 2016/0089015 A1    Mar. 31, 2016

(30) Foreign Application Priority Data
Sep. 25, 2014   (DE) .................. 10 2014 113 901

(51) Int. Cl.
*A61B 3/00*   (2006.01)
*A61B 3/10*   (2006.01)
(Continued)

(52) U.S. Cl.
CPC ............ *A61B 3/0025* (2013.01); *A61B 3/102* (2013.01); *A61B 3/1225* (2013.01); *A61B 3/13* (2013.01);
(Continued)

(58) Field of Classification Search
CPC ..... A61B 3/0025; A61B 3/102; A61B 3/1225; A61B 3/13; A61B 3/14; A61B 90/20;
(Continued)

(56) References Cited

U.S. PATENT DOCUMENTS

2012/0063660 A1   3/2012  Imamura et al.
2012/0080612 A1*  4/2012  Grego ............... G02B 26/0858
                                                  250/458.1
(Continued)

FOREIGN PATENT DOCUMENTS

EP    2 189 110 A1    5/2010
WO   WO 2012/100030 A2   7/2012

OTHER PUBLICATIONS

Bouget, David, et al., "Surgical Tools Recognition and Pupil Segmentation for Cataract Surgical Process Modeling," *Medicine Meets Virtual Reality—NextMed*, 7 pgs. (Feb. 2012).
(Continued)

*Primary Examiner* — Jie Lei
*Assistant Examiner* — Mitchell Oestreich
(74) *Attorney, Agent, or Firm* — Christensen, Fonder, Dardi & Herbert PLLC (57) ABSTRACT

A method for improving an OCT image of an object such as the retina of an eye, using optical coherence tomography by an imaging beam path. In order to suppress shadowing effects due to a surgical instrument moved in the imaging beam path, a time series of OCT images is produced. For an OCT image to be corrected, an area of the object lying in the image and shadowed by the instrument is determined. Another earlier OCT image in which the area of the object is not shadowed is searched in the time series. Image information for the area of the object is read from the earlier OCT image. A corrected OCT image is produced by inserting the read-image information into the OCT image to be corrected, wherein in the OCT image to be corrected, the image information replaces the area of the object which is shadowed by the instrument.

23 Claims, 4 Drawing Sheets (51) Int. Cl.
| | | |
|---|---|---|
| *A61B 3/12* | (2006.01) | |
| *A61B 3/13* | (2006.01) | |
| *A61B 3/14* | (2006.01) | |
| *A61B 90/20* | (2016.01) | |
| *A61B 5/00* | (2006.01) | |
| *A61B 5/055* | (2006.01) | |
| *G02B 9/02* | (2006.01) | |
| *G02B 21/36* | (2006.01) | |
| *G06T 5/00* | (2006.01) | |
| *G06T 5/50* | (2006.01) | |
| *A61B 34/20* | (2016.01) | |
| *A61B 90/00* | (2016.01) | |
| *G01B 9/02* | (2006.01) | |

(52) U.S. Cl.
CPC .............. *A61B 3/14* (2013.01); *A61B 5/0035* (2013.01); *A61B 5/0066* (2013.01); *A61B 5/055* (2013.01); *A61B 5/7217* (2013.01); *A61B 90/20* (2016.02); *G01B 9/0203* (2013.01); *G01B 9/02087* (2013.01); *G01B 9/02089* (2013.01); *G01B 9/02091* (2013.01); *G02B 21/367* (2013.01); *G06T 5/005* (2013.01); *G06T 5/50* (2013.01); *A61B 2034/2055* (2016.02); *A61B 2090/3735* (2016.02); *G06T 2207/10101* (2013.01)

(58) Field of Classification Search
CPC ..... A61B 5/0035; A61B 5/0066; A61B 5/055; A61B 5/7217; A61B 2034/2055; A61B 2099/3735; G01B 9/0203; G01B 9/02087; G01B 9/02089; G01B 9/02091; G02B 21/367; G06T 5/005; G06T 5/50; G06T 2207/10101
USPC .......................................................... 351/206
See application file for complete search history.

(56) References Cited

U.S. PATENT DOCUMENTS

| | | |
|---|---|---|
| 2012/0184846 A1 | 7/2012 | Izatt et al. |
| 2012/0200824 A1 | 8/2012 | Satake |
| 2013/0197357 A1 | 8/2013 | Green et al. |
| 2013/0208129 A1 | 8/2013 | Stenman |
| 2014/0024949 A1 | 1/2014 | Wei et al. |
| 2014/0100439 A1* | 4/2014 | Jones ................ G06T 7/0016 600/407 |
| 2014/0100440 A1 | 4/2014 | Cheline et al. |
| 2015/0223771 A1* | 8/2015 | Lee ..................... A61B 6/541 382/131 |

OTHER PUBLICATIONS

Sznitman, Raphael, et al., "Unified Detection and Tracking of Instruments During Retinal Microsurgery," *IEEE Transactions on Pattern Analysis and Machine Intelligence*, vol. 35, No. 5, pp. 1263-1273 (May 2013).

Tao, Yuankai K., et al., "Microscope-integrated intraoperative OCT with electrically tunable focus and heads-up display for imaging of ophthalmic surgical maneuvers," *Biomedical Optics Express*, vol. 5, No. 6, pp. 1877-1885 (May 20, 2014).

* cited by examiner

METHOD FOR CORRECTING AN OCT IMAGE AND COMBINATION MICROSCOPE

PRIORITY CLAIM

The present application claims priority to German Patent Application No. 102014113901.1, filed on Sep. 25, 2014, which said application is incorporated by reference in its entirety herein.

FIELD OF THE INVENTION

The invention relates to a microscope for imaging an object and an image-processing apparatus and a method for improving an OCT image of the object, in particular the retina of an eye.

BACKGROUND

A surgical microscopy system in which an OCT system is integrated is known from WO 2012/100030 A2. It images an object field optically. The image can be observed via eyepieces of an optical imaging system. The OCT system scans the object field and carries out measurements by means of optical coherence tomography. This surgical microscopy system is used in particular for imaging the eye, both optically and by OCT images, during a surgical procedure on the eye. During surgery a surgical instrument may happen to shadow parts of the image. To suppress shadowing effects in the OCT image, a time series of OCT images is produced and averaged. Movements of the instrument in front of the object and the shadowing effects caused by the instrument are suppressed in the averaged image.

A similar surgical microscopy system which likewise provides for a combination of optical microscopy and OCT imaging possible is known from US 2014/0024949 A1. Supporting shadows is not an issue in this publication.

From US 2013/0208129 A1 a method for digital image enhancement is known. To improve noise properties, the signal of single pixels are subjected to a threshold analysis. Data of pixels having a noise above the threshold are replaced by data from pixels of earlier taken pictures having noise properties below the threshold.

SUMMARY OF THE INVENTION

The object of the invention is to provide a method and a combination microscope to better suppress shadowing effects due to an instrument moved in the imaging beam path.

The invention provides a method for improving an OCT image of an object, in particular the retina of an eye, wherein a time series of OCT images is provided by optical coherence tomography. For an OCT image to be corrected, an area of the object which is shadowed by the instrument is detected in this OCT image. Another, in particular earlier, OCT image is searched for in the time series in which earlier OCT image the detected area of the object must not be shadowed by the instrument. Image information for the area of the object is read from this earlier OCT image and a corrected OCT image is produced by inserting the read image information into the OCT image to be corrected, wherein in the OCT image to be corrected the image information replaces the area of the object which is shadowed by the instrument.

The invention further provides a microscope for imaging an object, in particular the retina of an eye, wherein the microscope has an imaging beam path to image the object by means of optical coherence tomography and comprises an image-processing apparatus which records a time series of OCT images. In order to suppress shadowing effects due to an instrument, in particular a surgical instrument, moved in the imaging beam path, the image-processing apparatus detects an area of the object in an OCT image to be corrected, which area is shadowed by the instrument. The image-processing apparatus further searches the time series for another, in particular earlier, OCT image in which the detected area of the object is not shadowed by the instrument, reads, from this earlier OCT image image information for the detected area of the object and produces a corrected OCT image by inserting the read image information into the OCT image to be corrected, wherein the image information replaces the detected area of the object in the OCT image to be corrected. The invention additionally provides an image-processing apparatus having these properties.

The invention provides for a correction of image errors in OCT microscopy or an OCT microscope, which image errors occur due to the fact that regions of the image are shadowed by an instrument which is moved in the imaging beam path. This instrument may be a surgical instrument. The invention suppresses the effect of a shadow in the OCT image in that another OCT image in which the area affected by the shadowing effect is not shadowed by the instrument is looked for in the time series of OCT images. For this detected area, the image information of the other OCT image is used in order to improve the image to be corrected in respect of the shadowing effect. This image correction is far better than averaging known from the state of the art because only items of image information which were not impaired by the shadowing effect due to the instrument are combined. A user thus obtains the maximum image quality in all image areas, even in those that are located in the shadow of the instrument. A significant difference to the concept of US 2013/0208129 A1 is that the invention does not examine noise in the image but detects whether parts of the OCT image is shadowed by the instrument. Such shadowing does not generate noise in the image, i.e., one would not be able to detect it by the concept of US 2013/0208129 A1. Furthermore, the substituting information of the shadowed areas are not found by searching for images having special noise properties but searching for images which contain the respective errors not-shadowed by the instrument.

Embodiments detect the shadowing by making a threshold analysis. However, the threshold or reference value used in this analysis is not connected with image noise. These embodiments select the reference value used in the threshold analysis such that the shadow of an instrument, i.e., of the surgical instrument, is detected. It is preferred for these embodiments to use an automatic search of shadowed areas and to utilize a reference value which is selected such that a shadow cast by the instrument is detected.

In this description the term "shadowing effect" or "shadow" refers to the shadow cast by the instrument during the OCT imaging, i.e., in the OCT image. The area of the object which is affected by the shadow is referred to as "shadowed area" or "detected area". In case of a combination microscope which combines optical microscopy and OCT microscopy, as a rule, location and/or size of the shadow which the instrument casts in the OCT image may not be identical to the shadow of the instrument in the optical image. This applies quite particularly to the imaging of the retina of an eye as there a grazing illumination, which is incident at an entirely different angle from the radiation in the OCT imaging, is usually used in the optical imaging.

Naturally, a shadow only occurs in the OCT image when the instrument is not transparent, or not sufficiently transparent, for the radiation which is used to produce the OCT image. The term "instrument" therefore means in this description any item which partially or fully absorbs the radiation used for producing the OCT image.

The method according to the invention detects the shadow in the OCT image due to the instrument. However, even in the case of images of human tissue, this does not necessarily require that this is carried out during a surgical procedure although it is possible to do so. Instead the method may also be carried out on already produced OCT images chronologically after a surgical procedure or on OCT images of dead tissue or technical material. It is possible to carry out the method on OCT images already produced and provided.

The method or the image-processing apparatus searches the time series for at least one other, usually earlier, image in which the area of the object which is shadowed in the image to be corrected is not shadowed by the instrument. For the case of an instrument constantly stationary during the time series, there is no such other image. In such case the method terminates with an error message or the image-processing device marks the shadowed area in the uncorrected image, for example, by a blackening, etc.

A marking is also possible if the method successfully carries out the image improvement or the image-processing device produced a corrected, thus improved, OCT image. In this way a user learns which areas of the corrected OCT image may possibly contain out-of-date image information. In embodiments of the method it is therefore preferred that the area of the object for which the image information was inserted is marked in the corrected OCT image. Analogously, it is preferred for embodiments of the image-processing apparatus or the combination microscope that in the corrected OCT image the image-processing apparatus marks the area of the object in which the image information was inserted or substituted.

This marking can be refined in further embodiments of the invention to provide an indication of the time interval between the OCT image to be corrected, in which the substitution or insertion took place, and the other OCT image, from which the inserted information originated. In preferred embodiments this indication can comprise a marking, in particular a greyscale or color representation of the image area into which the information is inserted. Thus, it is possible, for example, in the case of a black-and-white representation, to design the inserted area with an increasingly lower contrast, or with increasingly lower brightness/blackness, as the time interval increases. An observer thus intuitively perceives that the image information in this section of the image is less reliable, because it is less up-to-date.

During the search for the earlier OCT image in which the detected area of the object is not shadowed, a preferred embodiment chooses from several such images the other OCT image that has the smallest time interval to the OCT image to be corrected. In many cases the other image is chronologically older than the image to be corrected and, where several other images come into consideration, the most recent of these other earlier images is selected, preferably.

Other embodiments produce a correction information image additionally which indicates the area of the object in which the image information was inserted during correction. This can be a greatly simplified OCT image of the object in which the area in which the information is inserted is marked.

The invention can preferably be used in the case of the combination of optical microscopy and OCT imaging, e.g., in the microscope according to US 2014/0024949 A1. In such embodiments, the position of the instrument, and thus the position of the area of the object which is shadowed in the OCT image, can be detected by evaluating the optical image. Thus, preferred embodiments additionally provide optical images of the object and the position of the instrument during OCT imaging and the area of the object which is covered by the instrument shadow in the OCT image is detected from the optical image. The corresponding embodiments of the microscope comprise a camera which produces optical images of the object and provides optical image data, wherein the image-processing apparatus reads the optical image data assigned to the OCT image to be corrected, determines the position of the instrument in the optical image and, from this, detects the area of the object which is shadowed by the instrument in the OCT image to be corrected.

For improving the OCT image in the case of continuous OCT imaging and to have the image information for the areas of the object affected by the shadowing effect of the instrument in the OCT image available as economically in terms of computation and as quickly as possible, further embodiments produce a sequence of optical images in parallel to the time series of OCT images and to determine, from each image of the sequence a specification of location and size of the area of the object which is shadowed by the instrument in the OCT image. When the method for improving an OCT image is carried out afterwards, embodiments provide that a sequence of optical images is made available which was produced in parallel to the time series of OCT images, wherein each optical image is assigned to one of the OCT images. Then a sequence of specifications of the area of the object which is shadowed by the instrument in the OCT image is determined from the sequence of optical images and assigned to the OCT images.

In this way a most recent one of the other OCT images can be found very quickly. The search usually requires only to find the most recent OCT image in which the shadowed area of the object is not shadowed. Because of the information about the area of the object which is shadowed by the instrument in the OCT image, which is present for each OCT image from the time series, the search is particularly quick and economical in terms of computation.

Naturally, the invention is not limited to improving the OCT image in respect of only a single instrument. It is equally possible to also carry out the improvement for several instruments, for example, two instruments cooperating during a surgical operation, etc.

The method can be used during the imaging, thus online. Those embodiments comprise: a method for imaging an object, in particular the retina of an eye, wherein an OCT image of the object is produced by optical coherence tomography and a time series of OCT images is produced, wherein, to correct OCT images for a shadow cast by an instrument moved in an OCT imaging beam path during OCT imaging an OCT image to be corrected is selected, an area of the object lying in this OCT image is determined which is shadowed by the instrument, another OCT image in which the area of the object is not shadowed by the instrument is looked for in the time series, image information for the area of the object is read from this other OCT image and a corrected OCT image is produced by inserting the read image information into the OCT image to be corrected, wherein in the OCT image to be corrected the read image information replaces the area of the object which is shadowed by the instrument.

It is understood that the features mentioned above and those yet to be explained in the following are applicable not only in the stated combinations, but also in other combinations or singly, without departing from the scope of the present invention.

The invention is explained in more detail below by way of example with the aid of the attached drawings, which also disclose features essential to the invention. There are shown in.

BRIEF DESCRIPTION OF THE FIGURES

DETAILED DESCRIPTION

Figure 1:
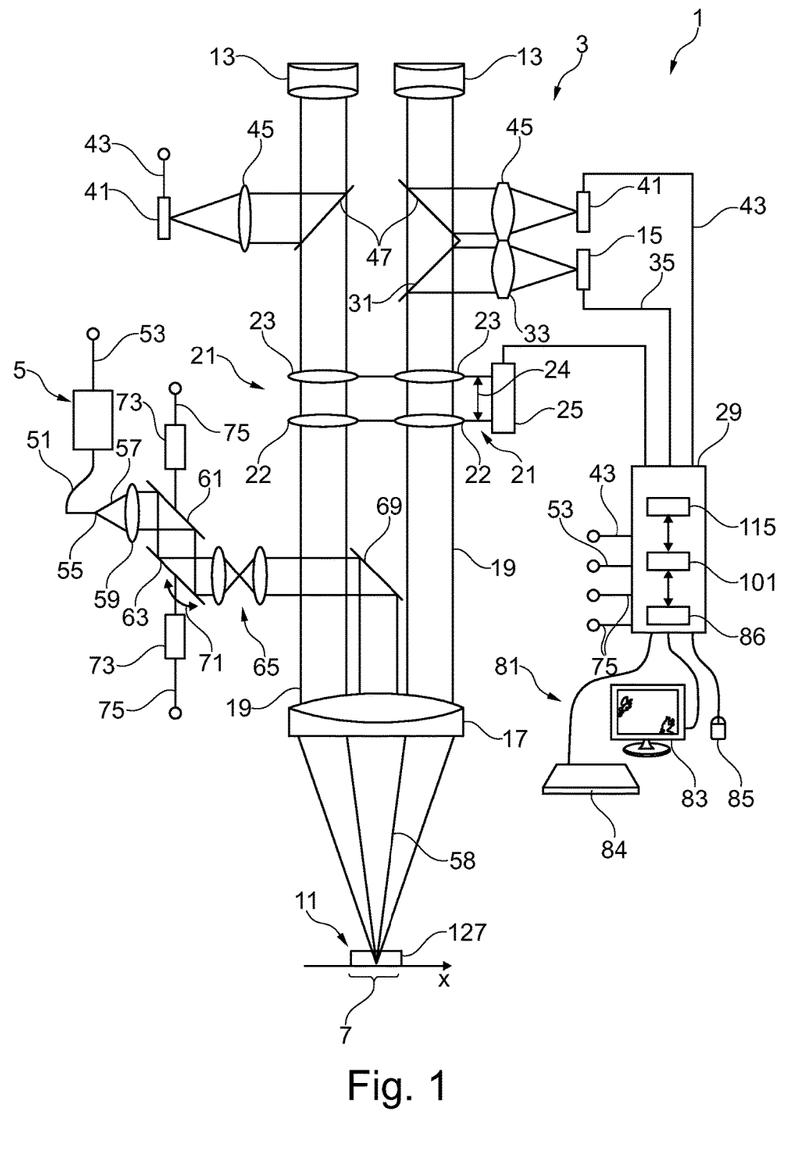
FIG. 1 a schematic representation of a microscopy system.

A microscopy system 1 represented schematically in FIG. 1 comprises an imaging lens system 3 and an OCT system 5. The microscopy system 1 is a combination microscope, e.g., a surgical microscope.

The imaging lens system 3 images an object 7 in an object field 11 on the one hand onto an eyepiece 13 and on the other hand onto a camera 15. The imaging lens system 3 comprises an objective lens 17 which can consist of one or more lens elements and, in the example represented here, images the object field 11 into a parallel beam path. In the beam path behind the objective lens 17 two beam bundles 19 are guided through a zoom lens arrangement 21 in each case which can change an image scale of the imaging lens system 3. The two zoom lens arrangements each have at least two lens groups 22, 23 which are movable relative to each other in the beam direction of the bundles 19, as indicated by an arrow 24 in FIG. 1. The movement of the two lens groups 22, 23 relative to each other is brought about by an actuator 25 which is controlled by a control apparatus 29 via a control line 27 to set the image scale of the imaging lens system 3.

After passing through the zoom lens arrangements 21 the beam bundles 19 enter the eyepiece 13. From the beam bundle 19 shown on the right in FIG. 1, a semi-reflecting mirror 31 couples out a part of the radiation. It is guided, via a camera adapter lens system 33, onto the camera 15, with the result that the latter detects an optical image of the object 7. Optical image data produced by the camera 15 are transmitted, via a data line 35, to the control apparatus 29.

In the embodiment shown the imaging lens system 3 comprises two (in principle optional) electronic display apparatuses 41 which are supplied with display image data by the control apparatus 29 via data lines 43. Display images produced by the display apparatuses 41 are in each case projected, via a projection lens system 45 and semi-reflecting mirrors 47 arranged in the beam bundles 19, into the beam paths towards the eyepieces 13, with the result that a user looking into the eyepieces 13 can perceive the images represented by the display apparatuses 41 superimposed with the image of the object 7.

The OCT system 5 comprises a low-coherence light source suitable for producing OCT image information (white light source) and an interferometer, which are represented only schematically as a block in FIG. 1. Via an optical fiber 51, the OCT system 5 emits OCT illumination radiation 57 which can impinge on an object to be measured. OCT measurement radiation coming back from the object in the opposite direction is coupled in at the optical fiber 51.

The OCT illumination radiation 57 exiting from one end 55 of the optical fiber 51 is collimated into an OCT illumination beam 58 by a collimator lens system 59, is deflected at two deflection mirrors 61 and 63, passes through a projection lens system 65, impinges on a mirror 69 and is directed from the latter, through the objective lens 17, onto the object field 11. The OCT measurement radiation reflected by the object 7 arranged in the object field 11 passes, in the reverse direction, through the objective lens 17, the projection lens system 65 and the collimator lens system 59 and is coupled into the optical fiber 51.

The OCT system 5 evaluates the OCT measurement radiation interferometrically by means of the interferometer and produces an OCT image, as a so-called A-scan, B-scan or C-scan depending on the scanning principle, yet to be explained. The OCT system 5 is controlled, via a control and data line 53, by the control apparatus 29, and the latter also receives the OCT image data from the OCT system 5 via this line.

The mirrors 61 and 63 are pivotable, in order to deflect the OCT illumination beam 58 onto different locations in the object field 11 and to collect the OCT measurement radiation from these locations, thus to at least partially scan the object field 11 by means of the mirrors 61, 63. As indicated by an arrow 71, the mirror 63 acts as a scanning mirror in the x-direction (horizontal direction in FIG. 1), the mirror 61 acts as a scanning mirror in the y-direction (perpendicular to the plane of drawing in FIG. 1). The mirrors 61 and 63 are set by actuators 73 which are controlled by the control apparatus 29 via control lines 75. The control apparatus 29 can thus guide the OCT measurement beam along a settable scanning path over the object field by corresponding control of the actuators 73.

In an embodiment the control apparatus 29 comprises a graphical user interface 81 which has a screen 83 as the representation medium, a keyboard 84 and a mouse 85 as the input media and a module 86 for controlling the microscopy system 1, which e.g., runs as a software module in the control apparatus 29.

The operation of the OCT system 5 is of no further importance for the image improvement explained in the following. In particular, the OCT system 5 can be formed as SS-OCT, SD-OCT, FT-OCT or TD-OCT, as known for OCT systems in the state of the art. The OCT system 5 produces a depth-resolved image 127 of the object 7 in the object field. Because of the interferometric principle of the OCT system 5, at each point of impingement of the OCT illumination beam 58, from which the OCT measurement radiation is also collected, a depth-resolved image 127 is produced which, however, is only one-dimensional if the point of impingement is not shifted, thus provides depth information along the optical axis which is predetermined by the setting of the deflection mirrors 61 and 63. Such a one-dimensional image is called an A-scan. If the point of impingement of the OCT illumination beam 58 is deflected along a line, a linear image 127, which is called a B-scan, results. If this line is shifted transverse to the line direction, a volume image or a so-called C-scan is obtained. The image 127 is then de facto a 3D resolution of the object 7 in the area which is scanned due to the adjustment of the deflection mirrors 61 and 63.

In the embodiment shown in FIG. 1, the surgical microscope 1 has, in addition to the module 86 which controls the basic functions of the microscopy system 1, also an optical image module 101 as well as an OCT image module 115. The optical image module 101 receives image data from the camera 15 and provides an optical image. The OCT image module 115 receives OCT image data from the OCT system 5 and provides an OCT image. OCT image module 115 and optical image module 101 continuously produce the corresponding images, with the result that a time series of OCT images and a sequence of optical images are available, which were obtained in each case simultaneously in a preferred embodiment, with the result that each OCT image from the time series in each case corresponds to an optical image from the succession. The image modules 101 and 115 store these time series and a user can retrieve them via the graphical user interface 81.

When the microscopy system 1 is used as a surgical microscope, a surgical instrument is used to manipulate the object 7. This surgical instrument is an example of an instrument which is moved in the beam path between object 7 and objective lens 17, in the case of eye surgery even within the object 7, for example, in the area of the retina.

Figure 2:
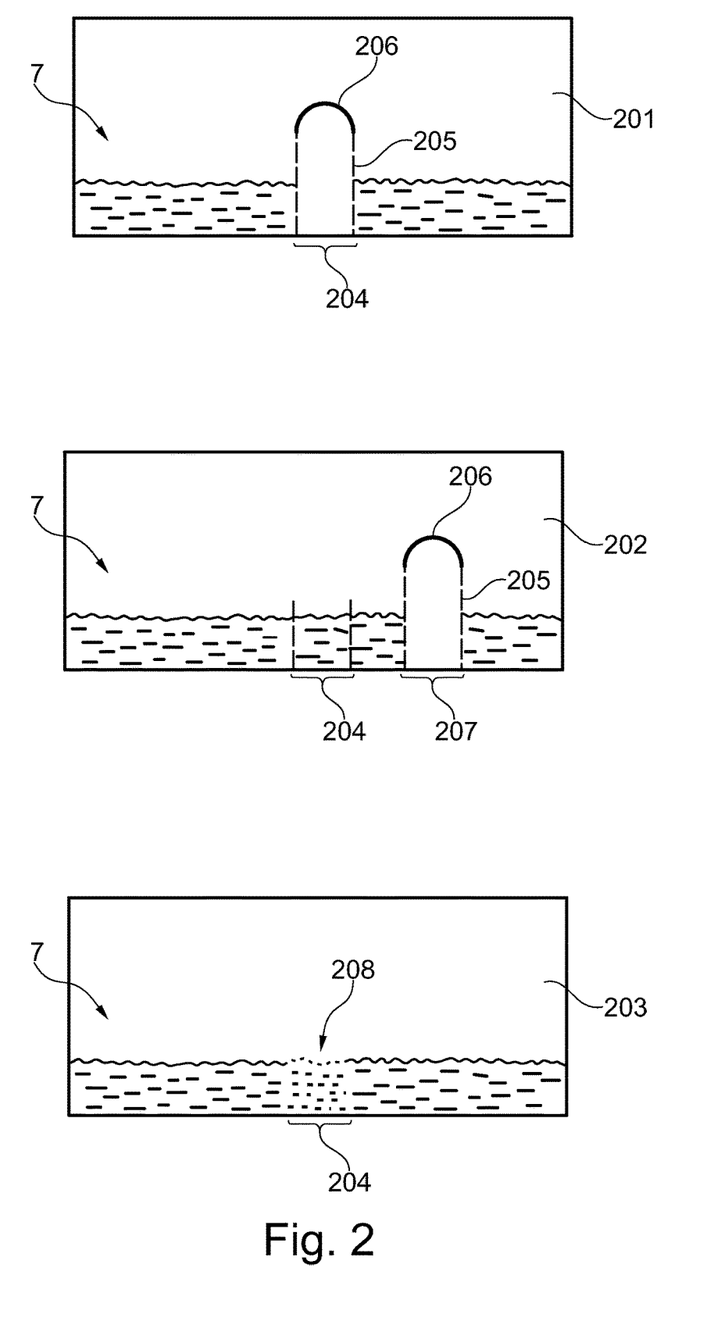
FIG. 2 a schematic representation of three OCT images which are produced with the microscope 1 of FIG. 1 and are improved in respect of the shadowing effect due to an instrument moved in the imaging beam path, FIG. 3 a correction information image which indicates the areas affected by image improvement, FIG. 4 a block diagram relating to a method for image improvement and FIG. 5 a flow chart of the method for image improvement.

FIG. 2 shows three OCT images one above another, in which an instrument 206 is an issue. In the top image of FIG. 2 an up-to-date OCT image 201 is represented which shows a sectional representation of the object 7. A boundary surface (symbolized by a wavy line) and deeper layers (symbolized by dashes) can be seen. Instrument 206 is located in the OCT image 201. It is not transparent for the OCT illumination radiation 58. As a result, the instrument 206 casts a shadow 205, which covers an area 204 of the object 7. In this shadowed area 204 there is no information in the OCT image. Instead, only the boundary surface of the instrument 206 facing the objective lens 7, but no deeper layer, is seen. The top image of FIG. 2 is, therefore, selected as OCT image 201 to be corrected, which is to be corrected in respect of the shadowing effect of the instrument 206.

The control apparatus 29 searches for another OCT image 202 in the time series provided by the OCT image module 115. The control apparatus 29 may comprise search dedicated modules (not represented further in FIG. 1), e.g., software modules. In case of an online operation, the other OCT image 202 is an older OCT image, i.e., an OCT image which was taken prior to the OCT image 201 to be corrected. The other OCT image which is looked for by the control apparatus 29 is characterized in that it shows the object 7 without shadow in the shadowed area 204. This is represented in the middle image of FIG. 2 by way of example as a situation in which the instrument 206 lies at different locations in the other OCT image 202 and in the OCT image 201 to be corrected. Any area 207 shadowed in the other OCT image 202 must not be identical to (minimum requirement) or not at all overlap with (optimum requirement) the area 204 of the object 7 which is shadowed in the OCT image 201 to be corrected.

The control apparatus 29 reads image information 208 for the shadowed area 204 from the other OCT image 202 and inserts it into the OCT image 201 to be corrected at the location of the shadowed area 204. In this way, it generates a corrected OCT image 203, the area 204 of which possesses substituted image information 208 which originates from the other OCT image 202.

In the embodiment shown in FIG. 2 the control apparatus 29 additionally removes the boundary surface of the instrument 206 in the OCT image 201 to be corrected. This is optional.

The feature shown in the corrected image 203, according to which the substituting image information 208 is marked, for example, by a greyscale representation, is further optional. In the schematic drawing of FIG. 2 this marking is symbolized by dots in the substituted parts of the corrected OCT image 203. In a development of this embodiment the marking is carried out in such a way that it gives information on the time interval between the OCT image 201 to be corrected, which usually is an up-to-date OCT image in the case of online operation, and the other OCT image 202, from which the image information 208 was taken and forms substituted parts in the corrected OCT image 203. In this way a user, to whom the corrected OCT image 203 is displayed on the screen 83, for example, can simply and intuitively recognize that the imaging of the object 7 in the area 204 contains older items of image information.

The image correction shown in FIG. 2 can, as already mentioned, be carried out online, i.e., during ongoing production of the time series by the OCT module 115. In such case, the OCT image 201 selected for correction usually is an up-to-date OCT image. The image improvement can, however, also be carried out offline on a time series of OCT images captured earlier and stored. Then the image-processing apparatus acts on the stored OCT images accordingly.

The detection of the shadowed area 204 can be carried out exclusively from the OCT images which were provided, e.g., by the OCT image module 115. In an embodiment simplified in this way the microscopy system need not produce an optical imaging. In other words, all elements in the beam path above the mirror 69 can be dispensed with, even the optical image module 101.

Figure 3:
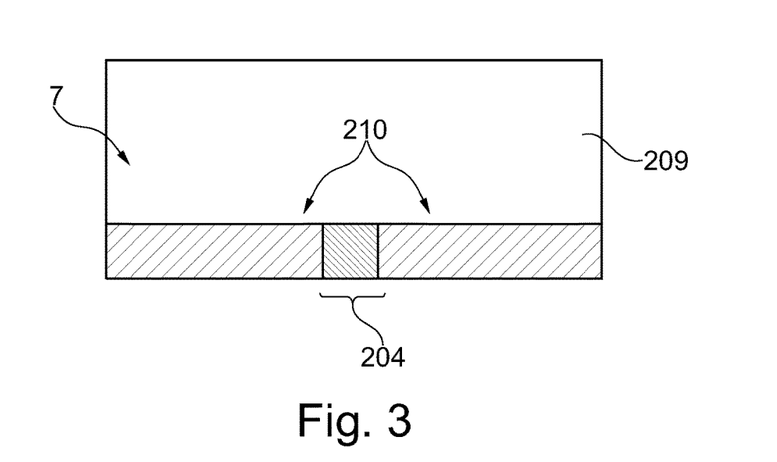

The marking of the substituted image information 208 informs a user about image areas having image information which may have a lower level of reliability because it originates from the other image 202, usually an older image. Such information can alternatively or additionally also be provided in that a supporting correction information image 209 is produced. The supporting correction information image 209 shows a simplified representation of the object 7, in which the area 204 in which the substituted image information 208 was used and the up-to-date areas 210 are marked differently. Additionally, the marking can encode the time interval between the other OCT image 202 and the corrected OCT image 201, for example, in a greyscale or color encoding.

A particularly preferred embodiment of the invention utilizes microscopy system 1, which, in addition to the OCT image, also provides an optical image of the object 7. The position of the shadow 205 of the shadowing instrument 206 and thus ultimately of the shadowed area 204 are detected from the optical image. This is advantageous because the optical image generally provides a higher resolution than the OCT image, which makes it possible to detect the shadowed area 204 at higher precision.

Figure 4:
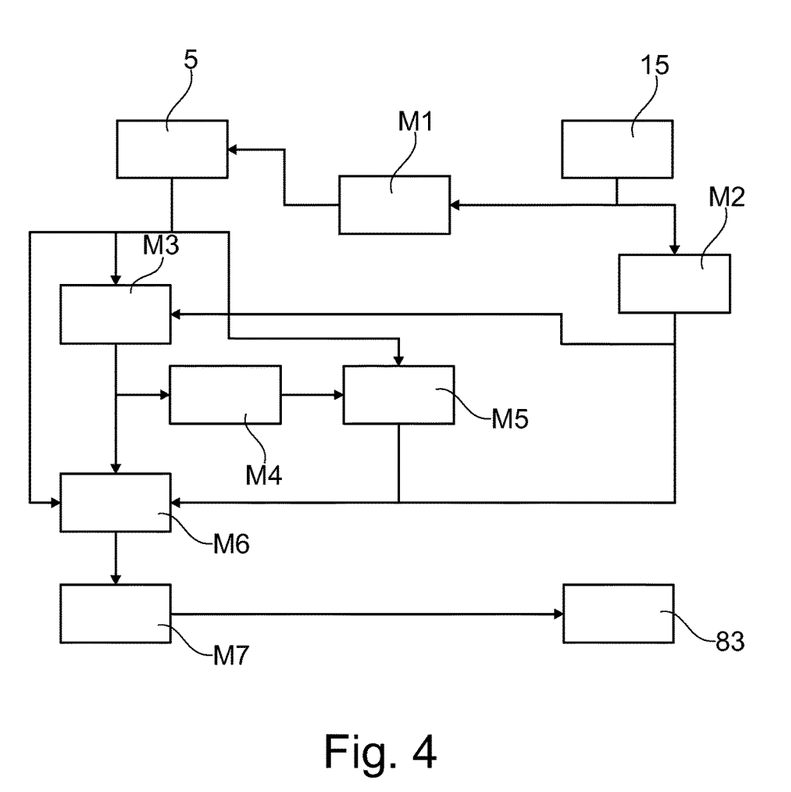

FIG. 4 relates to such a preferred embodiment, wherein elements which correspond to those of FIG. 1 are provided with the same reference numbers. In the block diagram of FIG. 4 the camera 15 is an example of the optical microscope which produces a sequence of optical images by means of the optical image module 101.

In a stabilization module M1 the sequence of optical images makes it possible, for one thing, to obtain an item of control information for the OCT system 5, which ensures, based on the optical image, that the OCT system 5 produces the OCT images at a desired and known location. This is advantageous because in most cases the OCT image has a much smaller extension than the optical image.

At the same time, an instrument-tracking module M2 detects movement of the instrument in the optical image. The instrument-tracking module M2 obtains from the optical image module 101 optical image data of the sequence of optical images. OCT image data is provided to a shadow-detection module M3, which additionally receives from the instrument-tracking module M2 information about the position of the optical instrument in relation to the OCT image. The shadow-detection module M3 detects the position of the shadow 205 and thus ultimately the shadowed area 204 in the OCT image.

The corresponding information is written to a storage module M4 which stores, among other things, the time series of image data. The storage module M4 holds, thus, a sequence of information on location and size of the shadowed area 204 in the OCT images. A registering module M5 registers the location of the shadowed area 204 in reference to the actual position of the OCT image.

A compensation module M6 receives from the registering module M6 the actual reference to the shadowed area 204 as well as from the storage module M5 the information on the different locations of shadowed area 204 in the time series of OCT images. Together with the data from the instrument-tracking module M2, the compensation module M6 thus searches, as already explained previously with reference to FIG. 2, the most recent other image 201 in which unshadowed image information exist for the shadowed area 204, and produces the corrected OCT image 203.

A display module M7 determines a time interval between the other OCT image 202 and the OCT image 201 to be corrected and marks the substituted image information 208 accordingly. It outputs the corresponding corrected image 203 (and, if produced, also the correction information image 209) on the screen 83.

FIG. 4 shows a block diagram of the method for improving an OCT image in respect of shadowing effects due to an instrument which is located in the imaging beam path of the OCT imaging. The method is started in step S0.

Figure 5:
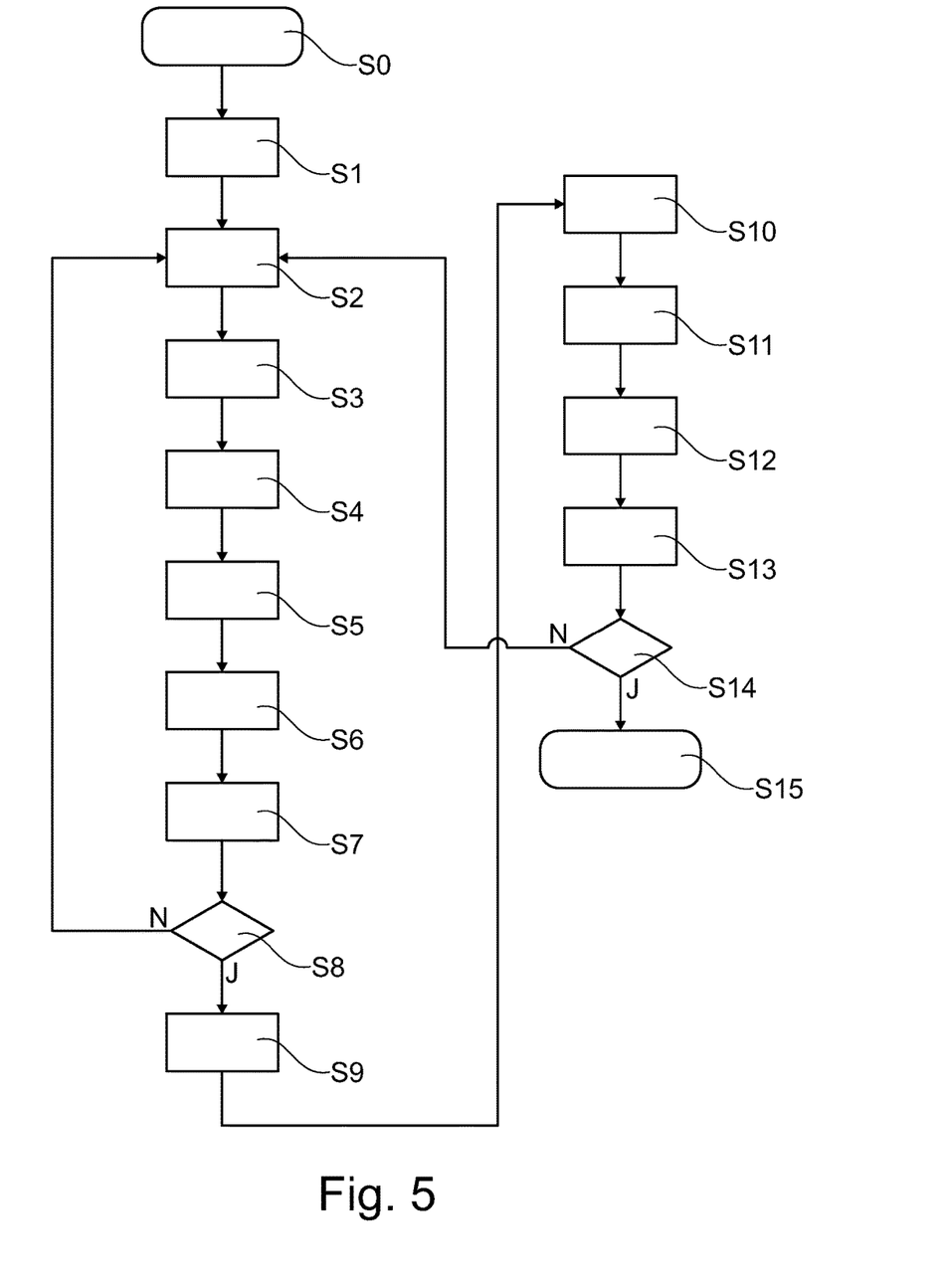

Step S1 provides a time series of OCT images, for example, by accessing a memory which, in online operation, buffers OCT images in a time series, or by reading a corresponding time series which was captured earlier in the case of an offline operation.

The OCT image 201 to be corrected is defined in step S2. In the case of an online operation it is usually the most up-to-date OCT image. The selection of the OCT image 201 to be corrected can, however, also be controlled by a user, which is expedient in particular in offline operation.

The optical image belonging to the OCT image to be corrected is recorded or read in step S3. After a position registering in step S4 between the optical image and the OCT image 201 to be corrected, step S5 searches the shadowing instrument in the optical image. Step S6 determines the position of the shadow in the OCT image 201 and the image area 204 affected by the shadowing effect. Step S7 then looks for an older image having a shadowed area 204 which is not or less shadowed. It may be pointed out here that an image improvement already takes place when another image 202 is found in which the area 204 is partially shadowed but is not completely shadowed. This already gives an improvement as the area 204 which is affected by the shadowing effect will be minimized, namely to an area in which area 207 of the other OCT image 202 overlaps with the area 204 of the OCT image 201 to be corrected.

A security query in step S8 checks whether such another image has been successfully found. After start of the method in online operation, a situation can arise in which the instrument 206 has not (yet) been moved. In this case, no image improvement is possible and a return is made to step S2 (N branch), provided that another image S2 to be corrected is selected there. In the case of an online operation this requirement can be met without trouble by the progressive capture of OCT images in the time series. In the case of an offline operation there already exists a time series of OCT images, with the result that, here too, the requirement to select another OCT image for the correction can be met in most cases.

However, if an older OCT image with an area 204 not completely shadowed is successfully found in step S7 (Y branch), the image information for this area 204 is read from the other OCT image 202 in step S9.

Step S10 overwrites, for the area 204, the image information in the OCT image 201 to be corrected, which was established in step S1, with the image information read for the area 204 from the other OCT image 202, which was found in step S7.

It may be pointed out that in a preferred embodiment, step S7 looks for the other OCT image 202 in as close in time to the OCT image 201 as possible.

The corrected OCT image 203 is produced by the insertion of the image information 208 into the area 204 of the OCT image 201 to be corrected. Step S12 determines the time interval between the other OCT image 202 and the OCT image 201 to be corrected, i.e., the difference in age between the image information 208 inserted into the area 204 and the remaining imaging of the object 7. This interval is then used in step S13 to mark the inserted image information 208 accordingly, wherein the marking indicates the difference in age, for example, by a greyscale or color encoding.

In step S14 an enquiry is made as to whether the method is at an end, i.e., whether further images are to be selected in step S2. If the method is not at an end (N branch), a return is made to step S2, again with the proviso of selecting a further OCT image 201 to be corrected. In the case where the method is at an end (Y branch), the method is ended in step S15.

The following modifications or amendments, or special embodiments, are possible:

As already mentioned, it is advantageous to carry out the detection of the shadow 205 and the detection of the area 204 affected in the OCT image by the shadowing effect in an optical image of the object 7 taken in parallel to the OCT image. Because of larger optical image fields the position of the shadowing instrument can be tracked. However, it is likewise possible to detect the location of the instrument directly from the OCT image, thus the area 204 affected by the shadowing effect.

The method can be carried out online and offline. In an online operation, up-to-date OCT images are improved by accessing the time series which contains earlier OCT images. In an offline operation, a time series which was captured earlier, for example, is made available. The method then need not be carried out in a microscope system 1, but can also be effected by a correspondingly programmed control apparatus. Even in offline operation it is possible to determine the position of the area 204 affected by the shadowing effect either in the OCT image or in an associated sequence of optical images.

The improvement of the OCT image was described previously with reference to a surgical microscope, and the shadowing instrument was mentioned as a surgical instrument. However, an application to not-living material is likewise possible, for example, in the case of an autopsy or the study of technical material. It has further been explained that the instrument is inserted into the object 7, while this is imaged with optical coherence tomography. In an embodiment the image improvement is likewise carried out when the instrument is located outside the object 7.

In the design according to FIG. 1, the microscope system is designed as a combination microscope. Although this simplifies the position recording of optical images and OCT images, the use of optical images to improve the OCT image is likewise also possible with separate microscopes which share fewer optical elements than is the case in the microscope system of FIG. 1, or none at all.

In the embodiment of FIG. 2, another OCT image 202 is looked for in which the area 204 affected by the shadowing effect is imaged completely. This is, as already mentioned, the optimum case because a corrected image 203 completely unimpaired by shadowing effect is then obtained. As already mentioned, an image improvement is also already achieved when another OCT image 202 is found in which the area 204 is shadowed but only partially. In a development it is possible to define a quality function which provides a weighing-up between the age difference of the other OCT image 202 and the OCT image 201 to be corrected and the level of un-shadowed coverage of the area 204 in the other OCT image 202. In this way a very old other OCT image 202 is prevented from being accessed for a complete replacement of the area 204 with image information 208 from the other OCT image 202. In a development this quality function can be set by the user, with the result that he can weigh up the importance of as complete as possible an imaging of the object 7 or as up-to-date as possible an imaging of the object 7 against each other.

In embodiments, an undesired old, other OCT image 202 is prevented from being used to obtain the image information 208 in the shadowed area 204 by defining a time window for the time series, within which the other OCT image 202 must lie in relation to the OCT image 201 to be corrected. The definition of such a time window supplements or replaces the use of the mentioned quality function.

In an embodiment, the method image processing device and the microscope according to the invention perform two analyzing steps. In a first step, an image to be corrected is analyzed whether there exist areas 204 of the imaged object 7 in the OCT image 201, which areas are shadowed by the instrument 206. This analyzing step involves a search for such shadowed areas 204. A second analyzing step searches for another OCT image 202 in the time series of OCT images, in which another OCT image the area 204 which was found in the first analyzing step is not shadowed by the instrument 206. This second step is a selecting step.

In embodiments, both analyzing steps involve a threshold analysis. For searching the area 204 shadowed in the OCT image to be corrected, a reference value is used which is selected such that the shadow of the instrument is detected. The second analyzing step, i.e., the search for the other OCT image 202 in which the area 204 is not shadowed by the instrument 206 uses a reference value for the threshold analysis which is selected such that it is detected whether the area 204 is not shadowed by the instrument 206. Other embodiments use the threshold analysis only for one of the two analyzing steps.

If a threshold analysis is used in both analyzing steps, the same reference value may be used. In embodiments, the reference value is a brightness or intensity reference value, and the intensity in the area 204 has to be below this value (first analyzing step) and above this value (second analyzing step). Whether the intensity in the image has to be above or below the reference value depends, of course, from the type of OCT image. If the OCT image is a negative image, the situation is inverted. Moreover, some embodiments use different reference values to establish a kind of hysteresis.

In some embodiments, both analyzing steps resort to an optical image of the object 7 to search for the shadowed area 204 in the image to be corrected and/or not-shadowed areas in the other image from which the image information for substitution in the image to be corrected are extracted. A threshold analysis can be used when analyzing the optical images, too. Of course, the relative position of optical image and associated OCT image, and in particular different viewing angles are to be taken into account to determine from the optical image the area which is shadowed in the OCT image. The location of the shadowed area can be stored or buffered as an additional information for each OCT image to support a later offline analysis. Alternatively, an optical image is stored for each OCT image to have the possibility to perform the whole procedure later, i.e., offline.

It goes without saying that a combination of threshold analysis and search in the optical image is possible in some embodiments. In particular, it is possible to perform the first analyzing step direct in the OCT image and the second analyzing step in optical images associated to the OCT images. A reversal is possible, i.e., the first analyzing step can analyze an optical image associated to the OCT image which has to be corrected and the second analyzing step can search OCT images.

Some embodiments select the source of the analyzing steps, i.e., whether optical images or OCT images are used, based on further information, in particular data defining the instrument or instruments which may cast the shadow.

The invention claimed is:

1. A method for improving an optical coherence tomography (OCT) image of an object, comprising:
    providing a time series of OCT images of the object, the time series of OCT images including an OCT image comprising an area of the object shadowed by an instrument that was moved in an OCT imaging beam path during generation of the time series of OCT images, the beam generated by an image-generating device, the beam exiting the image-generating device at an optical element located external to the object, and projecting through free space to the object, the instrument being independent of the image-generating device,
    selecting for correction, the OCT image that comprises the area of the object shadowed by the instrument,
    detecting the area of the object shadowed by the instrument in the OCT image to be corrected,
    searching and selecting from the time series of OCT images another OCT image comprising an image area corresponding to the area of the object shadowed by the instrument, wherein the corresponding image area is not shadowed by the instrument,
    extracting image information of the corresponding area of the object from the other OCT image, and
    producing a corrected OCT image by inserting the extracted image information into the OCT image to be corrected, wherein the extracted image information from the selected OCT image replaces image information of the area of the object shadowed by the instrument in the OCT image to be corrected.

2. The method according to claim 1, wherein the object is a retina of an eye and the instrument is a surgical instrument.

3. The method according to claim 1, wherein an area comprising the extracted image information is marked in the corrected OCT image.

4. The method according to claim 3, wherein an area of the object into which the extracted image information was inserted is encoded with respect to a time interval between the OCT image to be corrected and the selected OCT image.

5. The method according to claim 4, wherein the area of the object into which the image information was inserted is encoded by a greyscale or color representation.

6. The method according to claim 1, wherein an additional correction information image is produced which indicates the area of the object into which the extracted image information was inserted.

7. The method according to claim 1, wherein the object is additionally imaged optically and an optical image of the object is generated, wherein the optical image is assigned to the OCT image which was taken at a same time and the optical image shows the position of the instrument and wherein the area of the object shadowed by the instrument in the assigned OCT image to be corrected is detected in the optical image.

8. The method according to claim 7, wherein a sequence of additional optical images is provided which was produced in parallel to the time series of OCT images, each additional optical image is assigned to one of the OCT images of the time series and wherein in each optical image a location of a shadow cast by the instrument is detected and data specifying the shadowed area in the corresponding OCT images is generated to obtain for each OCT image of the time series a specification of the area shadowed by the instrument.

9. A microscope for imaging an object, comprising:
an OCT imaging beam path to image the object using optical coherence tomography (OCT), and
an image-processing apparatus which records a time series of OCT images, wherein:
the image-processing apparatus defines an OCT image, of the time series of OCT images, to be corrected for a shadow in the OCT image cast by an instrument that was moved in the OCT imaging beam during generation of the time series of OCT images,
the image-processing apparatus detects a shadowed area which is shadowed by the instrument in the OCT image to be corrected,
the image-processing apparatus searches the time series and selects another, OCT image in which an area corresponding to the shadowed area is not shadowed by the instrument,
the image-processing apparatus extracts image information for the area corresponding to the shadowed area from the selected other OCT image, and
the image-processing apparatus produces a corrected OCT image by inserting the extracted image information into the OCT image to be corrected, wherein in the OCT image to be corrected the extracted image information of the selected OCT image replaces image information of the shadowed area, and
wherein the beam is projected through free space from an optical element of the image-generating device to the object, the optical element located external to the object, the instrument being independent of an image-generating portion of the microscope.

10. The microscope according to claim 9, wherein the image-processing apparatus marks an area of the object comprising the extracted image information in the corrected OCT image.

11. The microscope according to claim 10, wherein the image-processing apparatus encodes the area of the object into which the extracted image information is inserted in respect of a time interval between the OCT image to be corrected and the selected OCT image.

12. The microscope of claim 11, wherein the encoding is a greyscale or color representation of the area of the object into which the image information is inserted.

13. The microscope according to claim 9, wherein the image-processing apparatus produces an additional correction information image which indicates the area of the object comprising the extracted image information.

14. The microscope according to claim 9, wherein the microscope comprises a camera which produces an additional optical image of the object and provides respective optical image data, wherein the image-processing apparatus reads the optical image data, detects a position of the instrument in the optical image and the area of the object which is shadowed by the instrument in the OCT image to be corrected.

15. The microscope according to claim 14, wherein the image-processing apparatus produces a sequence of optical images in parallel to the time series of OCT images and generates for each optical image a specification of the area of the object which is shadowed by the instrument in the associated OCT image.

16. An image processing apparatus for improving images of an object in a time series of optical coherence tomography (OCT) images wherein an instrument was moved in an OCT imaging beam path, the apparatus is configured to:
define an OCT image to be corrected for a shadow cast by the instrument in the OCT image, the instrument being independent of an image-generating device,
detect an area which is shadowed by the instrument in the OCT image to be corrected,
search and select in the time series another OCT image comprising an area corresponding to the area shadowed by the instrument, wherein the corresponding area is not shadowed by the instrument,
extract image information of the corresponding area from the selected OCT image, and
produce a corrected OCT image by inserting the extracted image information into the OCT image to be corrected, wherein the extracted image information replaces image information of the shadowed area in the OCT image to be corrected, and
wherein the beam is generated by the microscope and projected through free space from an optical element of the image-generating device to the object, the optical element located external to the object, the instrument being independent of the microscope.

17. The image-processing apparatus according to claim 16, wherein the image-processing apparatus marks in the corrected OCT image an area of the object comprising the extracted image information.

18. The image-processing apparatus according to claim 16, wherein the image-processing apparatus encodes an area of the object comprising the extracted information with respect to a time interval between the OCT image to be corrected and the selected other OCT image.

19. The image-processing apparatus according to claim 18, wherein the encoding is a greyscale or color representation of the area of the object comprising the extracted image information.

20. The image-processing apparatus according to claim 16, wherein the image-processing apparatus produces an additional correction information image which indicates an area of the object comprising the extracted image information.

21. The method of claim 1, wherein the instrument comprises an instrument used to manipulate the object.

22. The method of claim 9, wherein the instrument comprises an instrument used to manipulate the object.

23. The method of claim 16, wherein the instrument comprises an instrument used to manipulate the object.

* * * * *